United States Patent [19]

McDaniel

[11] Patent Number: 4,501,266

[45] Date of Patent: Feb. 26, 1985

[54] KNEE DISTRACTION DEVICE

[75] Inventor: John McDaniel, Warsaw, Ind.

[73] Assignee: Biomet, Inc., Warsaw, Ind.

[21] Appl. No.: 472,160

[22] Filed: Mar. 4, 1983

[51] Int. Cl.³ .................. A61F 5/00; A61B 17/00; A61B 17/18

[52] U.S. Cl. ..................... 128/69; 128/92 E; 128/303 R; 128/774; 128/782; 128/92 H

[58] Field of Search .............. 128/69, 75, 84 R, 84 B, 128/84 C, 92 R, 92 A, 92 E, 92 H, 303 R, 774, 782; 3/1.911

[56] References Cited

U.S. PATENT DOCUMENTS

| 3,976,060 | 8/1976 | Hildebrandt et al. | 128/92 R X |
| 4,024,860 | 5/1977 | Chelnokov et al. | 128/92 A X |
| 4,220,146 | 9/1980 | Cloutier | 128/69 |
| 4,364,389 | 12/1982 | Keller | 128/303 R |

FOREIGN PATENT DOCUMENTS 986392 1/1983 U.S.S.R. .............. 128/774

Primary Examiner—Ronald L. Frinks
Attorney, Agent, or Firm—Barnes & Thornburg

[57] ABSTRACT

A knee distraction device is provided for facilitating knee arthroplasty. An adjustable force calibration mechanism is disposed in the device to accommodate controlled selection of the ligament-tensioning force to be applied at respective opposite sides of the knee. In preferred embodiments, the tensioning force is provided by a screw-threaded connection with a calibrated compression spring interposed between the tensioning members. According to another preferred embodiment, fluid pressure is applied by means of a calibrated pressure valve to apply the ligament-tensioning force.

13 Claims, 5 Drawing Figures

KNEE DISTRACTION DEVICE

The present invention relates to a knee distraction device for facilitating knee arthroplasty, especially total knee arthroplasty.

One of the most important objectives in total knee arthroplasty of the type contemplated by the present invention is the restoration of the original anatomy of the patient's leg in extension. An important step in this process is to assure that not only are the bones of the leg properly aligned, but also that the ligament tension at both sides of the knee is balanced. Failure to restore the original anatomical relationships results in abnormally high stresses in the knee that lead to premature failure of the arthroplasty.

The mechanical axis of the leg is an imaginary line in the frontal plane that connects the head of the femur with the center of the ankle. This is the path the load takes between the torso and the floor during weight bearing. With a normal anatomy, the mechanical axis of the leg passes through the center of the knee. This assures that both condyles of the knee carry equal load. In the deformed arthritic patient, the mechanical axis passes to the side of the knee, thereby concentrating most of the load on one condyle.

The joint surface of the knee is spanned on both sides by the collateral ligaments. In the normal anatomy, the collateral ligaments are both equally tight in the extended leg. This tension in the collateral ligaments prevents sideways toggle (varus/valgus motion) of the leg. Additionally, the collateral ligaments help to limit anterior/posterior travel of the femur on the tibia. In the arthritic patient, a varus/valgus deformity often exists. This results in a stretched collateral ligament on the convex side of the deformity and a contracted ligament on the concave side.

To restore normal anatomical functions to the deformed knee, it is required to simultaneously:

(i) lengthen the contracted collateral ligament;

(ii) equally tension both collateral ligaments to such a degree that the extended knee resists anterior/posterior travel and varus/valgus forces and (iii) confirm that the mechanical axis of the leg passes through the knee.

After these requirements have been met, the femur and tibia are resected in anticipation of the thickness and shape of the prosthetic components. In this manner, when the natural articulating surfaces are replaced with the prosthesis, the anatomical relationships are properly maintained.

Historically, early knee instrumentation systems did not address the knee alignment, tension, and balance requirements of the extended leg. Stability was achieved by replacing the resected bone with a prosthesis thick enough to "shim up" the joint so that at least one collateral ligament was tight. Leg alignment and balancing of the collateral ligaments were secondary considerations.

Knee instrumentation later evolved to include a device inserted into the joint to separate the knee in extension so that the ligaments were stretched and the leg was aligned. Initially the leg was hand-held in this position, while the level of resection was established in anticipation of the prosthetic thickness. While this was an improvement over previous systems, the hand tensioning of the ligaments was not accurate and controllable. Furthermore, it was difficult to balance the tension of both collateral ligaments using this procedure.

The next improvement in instrumentation was the adoption of a device known generally as a knee distractor. The device comprises an instrument inserted between the bones at the opposite sides of the knee joint. Both compartments of the joint can be individually distracted with such a device until the mechanical axis of the leg is aligned over the knee and both collateral ligaments are tight and balanced. By distracting the joint mechanically rather than by hand, the tension and alignment are manitained securely while subsequent resection levels are established in anticipation of the prosthetic thickness. Exemplary of this type of instrumentation is the knee distractor unit marketed by Biomet, Inc., the assignee of the present application, under catalog number 446640. By way of further background information as to the environment of the invention, reference is hereby made to the Biomet, Inc. brochure entitled "A Common Sense Instrumentation Approach to Achieving Accurate Knee Replacement Alignment, Balance, and Collateral Ligament Tensioning," Form No. BMT-001-0482, April, 1982, the contents of which brochure are incorporated herein by reference thereto.

Although joint distractors presently available are useful and distinctly superior to the prior art, they still exhibit certain limitations with respect to the establishment of the level of distraction being applied across the knee and the establishment of the level of distraction being applied to each of the two collateral ligaments so that they can be balanced in tension. Generally, knee distractor devices are designed in such a way that the load is applied to cantilevered arms in each of the two knee compartments. The cantilevered loading causes considerable friction in the opening mechanism. This friction precludes adjusting the tension in each compartment according to the "feel" of the opening mechanism. Consequently, the surgeon must feel the collateral ligaments to get only a qualitative assessment of collateral ligament tension and balance. This assessment is further complicated by the fact that each collateral ligament consists of a group of fiber bands. For given tension across the knee, each individual fiber band will have varying amounts of tension. Therefore, an accurate assessment of collateral ligament tension requires considerable experience, reinforced with post-operative follow-up of the patient's stability.

The present invention concerns an improvement in knee distractors of the type described above. According to one aspect of the invention, a force gauge is interposed between the distraction force-applying mechanism and the distraction arms or members engageable with the respective leg parts. In this manner, a "calibrated" knee distractor is obtained.

The clinical application of the calibrated knee distractor of the present invention is as follows. The surgeon "dials in" a predetermined tension to each of the two compartments of the knee. This assures that not only is there the proper tension across the knee, but also balanced tension on both collateral ligaments. The tension is exact and not just qualitative. If, while the knee is held in proper tension, the mechanical axis of the leg passes through the knee, then proper anatomy has been restored. If, while the knee is held in proper tension, the mechanical axis does not pass over the knee, then the collateral ligament on the concave side of the leg must be lengthened until the proper anatomy has been restored.

A first major advantage of the calibrated knee distractor of the present invention is that it takes the guesswork out of the tensioning and balancing of the knee and simultaneously reduces the time involved for this part of the arthroplasty. A further advantage is that the increased accuracy of the calibrated knee distractor makes it possible to better diagnose a ligament contracture. Furthermore, in any case, the ability to load the knee with a predetermined load assures consistency from patient to patient and eliminates the learning curve involved with conventional distractors.

According to especially preferred embodiments, the calibrated knee distractor is designed with an ultra low-friction mechanism so that the limitations inherent in a knee distractor caused by friction are eliminated. With a low-friction device, the force generated by the force-applying mechanism is very close to the force available in the joint for tensioning ligaments. This not only facilitates the operation and application of the device, but also enhances the accuracy of the controlled calibration of the device.

A first preferred embodiment of the invention incorporates a threaded mechanism to apply distracting forces to the joint and a calibrated compression spring to act as a force gauge. A low friction linear bearing supports each of the distractor arms. This construction is especially advantageous in that a simple, reliable, lightweight construction is provided.

Another preferred embodiment is contemplated wherein the distraction force is applied by means of fluid pressure-actuated cylinders, with force measurement being accomplished by way of a calibrated pressure gauge.

These and further objects, features, and advantages of the present invention will become more obvious from the following description when taken in connection with the accompanying drawings which show, for purposes of illustration only, several embodiments in accordance with the present invention.

Figure 1:
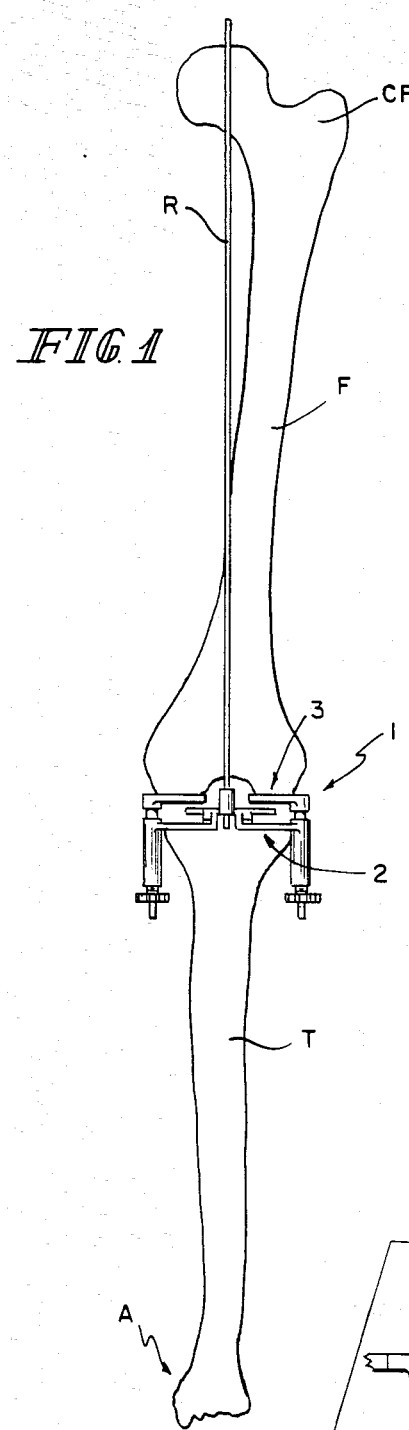
FIG. 1 is a frontal diagrammatic view showing a distractor device according to the invention positioned on the leg bones of a patient.

FIG. 1. schematically depicts the knee distractor of the present invention in position on a patient's leg in extension, with the femur F disposed above the tibia T. The distraction device 1 includes a tibia-engaging member 2 and a pair of femoral condyle-engaging members 3 which are separately adjustable vertically with respect to the member 2. In use, the bottom surface 2A of the tibial-engaging member 2 rests on the resected tibial plateau while the upper surface 3A of the condyle-engaging members 3 engage the respective condyles.

Figure 2:
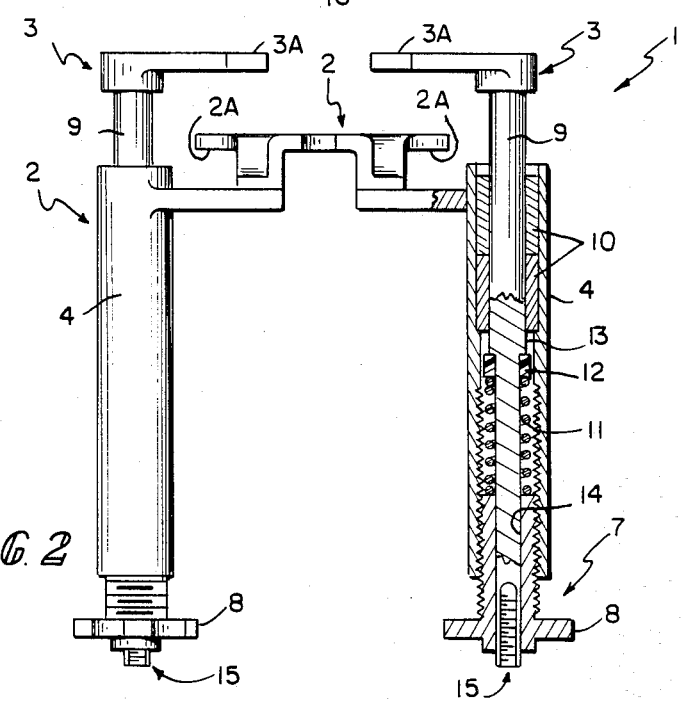
FIG. 2 is a frontal view of a knee distractor constructed in accordance with the present invention, with portions broken away.

The mechanism for adjustably forcing the members 2 and 3 apart is best illustrated in FIG. 2. A tubular member 4 is fixedly connected to the tibia-engaging part 2 and exhibits a lower internally threaded region which is threadably engaged with threads 6 of an externally threaded adjusting member 7. Adjusting member 7 includes a manual operating knob 8 for rotating the same.

The condyle-engaging member 3 is carried on a cylindrical shaft 9 which is slidably movable within the tube 4. To reduce sliding friction between the shaft 9 and the tube 4, linear ball bushings 10 are provided at the inside of the tube 4. A calibrating adjusting spring 11 is disposed inside of the tube 4 and has its lower end engageable with the threaded adjusting member 7 and its upper end engaged against Delrin polymer spacers 12, which in turn abut at shoulders 13 of the shaft 9. Delrin polymer is a polyformaldehyde of greater than 15,000 molecular weight sold by DuPont. The lower part of the shaft 9 extends downwardly as cut-away portion 14 through a hole centrally located in adjusting member 7, and includes force calibration markings 15 at its lower end which depict the relative position of the adjusting member 7 and the shaft 9 in a readily readable manner at its point of emergence below operating knob 8.

The application of the predetermined tension at the right-hand condyle-engaging member 3 (referring to the FIG. 2 right-hand illustration) is as follows. First, the tibia-engaging portion 2 is placed on the tibial plateau, and the patient's leg is placed in extension with the members 3 spaced from the facing condyles. The operating knob 8 is then rotated to effectively push the member 3 away from the member 2 and into contact with the condyles and then forcibly begin to tension the ligaments at the right-hand side of the knee. Since there is substantially no frictional resistance between the slidable shaft 9 and the tube 4, the compression spring 11 only begins to be compressed after a forcible engagement of the member 3 against the condyle. The operator can then rotate operating knob 8 to the desired compression spring force to be applied, and the member 3 will be correspondingly moved with the compression of the spring 11 corresponding to that selected and readable by the operator. Thus, irrespective of the initial distance between the condyle and the tibial plateau with relaxed ligaments, a predetermined, reliable application of force is obtainable with this arrangement. The left-hand condyle-engaging member 3 (as shown in FIG. 2) is operated in substantially the same way. If, when the same calibrated spring force is applied to the two sides of the knee, the distances between the tibial plateau and the condyles are different for the two sides of the knee, such that the mechanical axis of the leg is not correctly oriented, then appropriate adjustment of the ligament lengths is to be performed.

In particularly preferred embodiments, the knee distraction device is designed so that it can carry an alignment rod R (FIG. 1) for checking the alignment of the leg bone parts once the balanced ligament tensioning has been applied. In the illustration of FIG. 1, the rod R is disposed to pass through the middle of the knee joint by being disposed at the center of the knee distraction device 1 and should then extend to the center of the femoral head CF. The rod R should also be aligned with and can be moved downwardly through the holder at the distraction device 1 so that it passes through the center of ankle A. The frame connection for the tubes 4 and the tibial-engaging member 2 includes a slide guide arrangement schematially depicted at 16 for accommodating the detachable connection of the rod R, so as to facilitate a checking of the leg bone alignment after the ligament tension has been applied and balanced for both sides of the knee in the manner described above.

Figure 5:
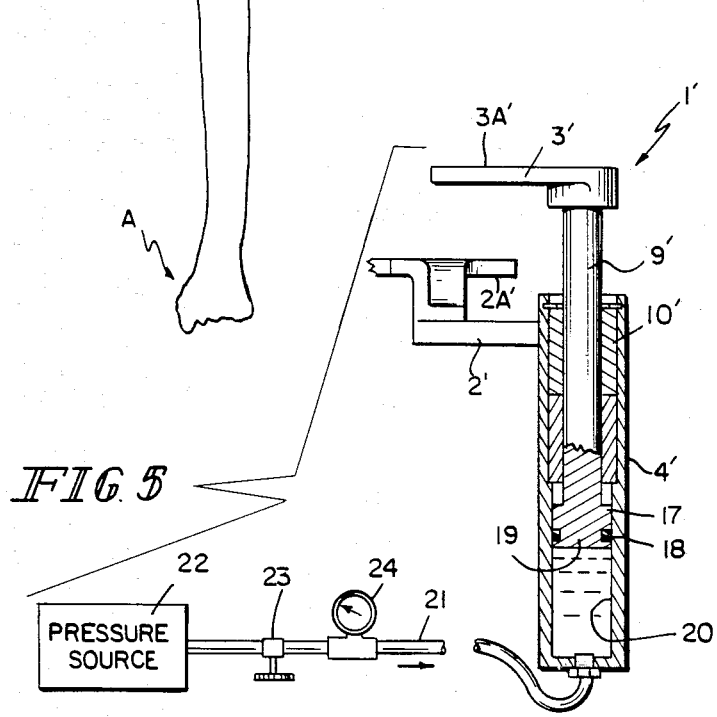
FIG. 5 is a partial frontal view showing a second preferred embodiment of the present invention, with protions broken away.

FIG. 5 depicts a modified embodiment for the force-applying and force-calibration device of a knee distractor constructed otherwise in the same manner as illustrated and described above with respect to FIGS. 2-4. In FIG. 5, only one side of the modified knee distractor device 1' is shown, with primed reference characters corresponding to like reference characters in the embodiment of FIGS. 2-4. In the FIG. 5 embodiment, the shaft 9' for the condyle-engaging member 3' is constructed at its lower end with a widened portion 17 bounded by a low-friction seal 18 so as to form a piston face 19 communicating with a cylinder space 20 formed by the lower portion of the tube 4'. Force is applied to the surface 19 by way of line 21 from a pressure source 22. A calibration valve 23 and pressure gauge 24 are provided in the line 21 for controlling the pressure of the fluid supplied to the space 20.

The operation of the FIG. 5 embodiment is as follows. In the same manner as for the embodiment of FIGS. 2-4, the tibial plateau-engaging member 2' is placed in position. Subsequently, very low pressure is applied via line 21 to cylinder space 20 to force the shaft 9' upwardly until tensioning of the ligaments begin. Subsequently, valve 23 is adjusted to the predetermined desired pressure force to be applied, moving the condyle-engaging member 3' to tension the ligaments to that force. Since there is very little frictional resistance to the relative movement of the shaft 9' in the tube 4' due to the linear ball bushings 10' and the minimal extra frictional force caused by the engagement of the seals 18 at the walls of the tube 4', substantially all of the fluid pressure forces are applied as ligament-tensioning forces. Although the predetermined ligament-tensioning force could be immediately dialed in on the valve 23, it is preferred to apply the low-pressure force to move the member 3' up to the position where the ligaments are just beginning to be tensioned. It is also contemplated with the embodiment of FIG. 5 that the threshold pressure for overcoming the friction resistance at seal 18 be considered in calculating the pressure force available for ligament tensioning.

Figure 3:
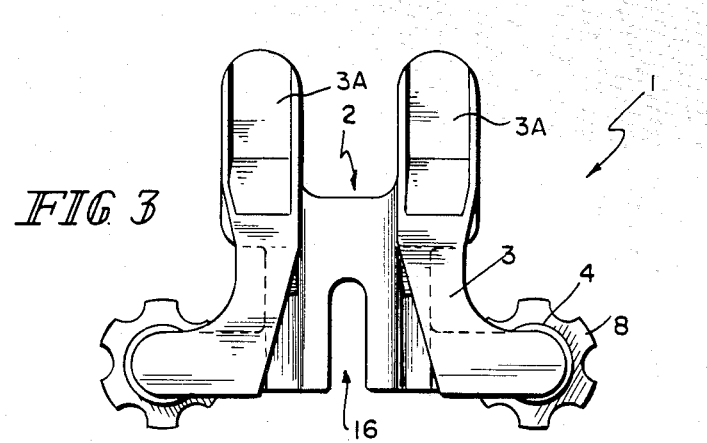
FIG. 3 is a top view of the knee distractor of FIG. 2.
Figure 4:
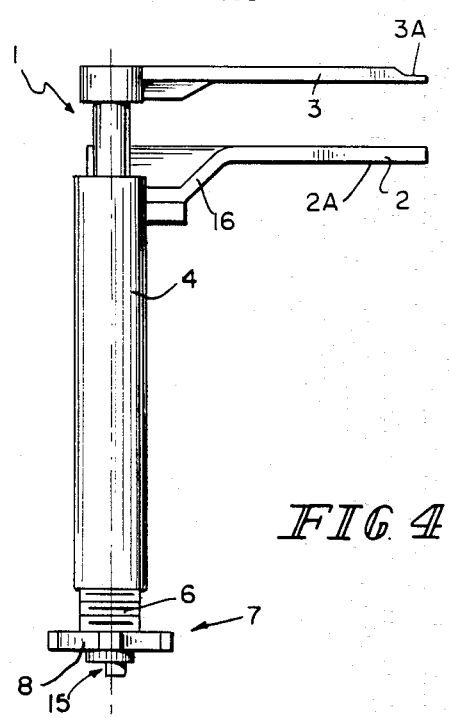
FIG. 4 is a side view of the knee distractor of FIGS. 2 and 3.

In the embodiment of FIGS. 2-4, an appropriate abutment stop connection may suitably be provided at the lower end of shaft 9 so as to prevent the same from being lifted upwardly out of the tube 4 when not in use engaged against a patient condyle.

Embodiments of the invention are also contemplated which include other than the tubular sliding guide connection of the tibia- and condyle-engaging members. One contemplated arrangement for minimizing the sliding friction effects provides for the arrangement of a pivot axle for the condyle-engaging member and the application of force at a position disposed at the opposite end of the pivot axle, so that the same operates in the manner of a see-saw, with minimal frictional resistance.

While I have shown and described several embodiments in accordance with the present invention, it is understood that the same is not limited thereto but is susceptible to numerous changes and modifications as would be known to those skilled in the art of the present disclosure and I therefore do not wish to be limited to the details shown and described herein but intend to cover all such changes and modifications as they are encompassed by the scope of the appended claims.

What is claimed is:

1. A knee distraction device for facilitating knee arthroplasty comprising
   a tibia-engaging member engageable with a resected tibial plateau of a patient,
   a condyle-engaging member engageable with a distal femoral condyle of the patient,
   force-applying means for forcibly moving said tibia- and condyle-engaging members relative to one another to tension the patient's ligaments,
   and adjustable force calibration means operatively connected with the force-applying means for calibrating the degree of ligament tension applied by the distraction device.

2. A knee distraction device according to claim 1 comprising
   two of said condyle-engaging members, one for each condyle of the patient's knee,
   wherein said force-applying means includes means for independently moving each of said condyle-engaging members relative to the tibia-engaging member, and wherein said calibration means includes means for independently calibrating the degree of ligament tension applied by the respective condyle-engaging members.

3. A knee distraction device according to claim 1 comprising slidably interengageable guide means for guiding the relative movement of the tibia- and condyle-engaging members.

4. A knee distraction device according to claim 3 wherein said calibration means includes calibration spring means interposed between the guide means.

5. A knee distraction device according to claim 4 wherein said slidably interengageable guide means includes two linear telescoping guide members fixedly attached respectively to the tibia- and condyle-engaging members, and wherein said calibration spring means is interposed between the telescoping guide members.

6. A knee distraction device according to claim 5 wherein one of said guide members is tubular-shaped and is fixedly attached to the tibia-engaging members and the other of said guide members is fixedly attached to the condyle-engaging member and is configured to slidably move along the inside of the tubular-shaped member,
   wherein the force-applying means includes a screw-threaded adjusting member, and wherein the calibration spring means is a compression spring interposed between the threaded adjusting member and the other of said guide members.

7. A knee distraction device according to claim 6 wherein low-friction lining means are provided in said tubular-shaped guide member to minimize the frictional resistance to relative sliding movement of the guide members with respect to each other.

8. A knee distraction device according to claim 7 wherein said low-friction lining means includes linear ball bushings.

9. A knee distraction device according to claim 8 further comprising a polyformaldehyde polymer spacer interposed between the calibration spring and the other of said guide members.

10. A knee distraction device according to claim 3 wherein said force-applying means includes means for applying fluid under pressure to move said tibia- and condyle-engaging members relative to each other.

11. A knee distraction device according to claim 10 wherein said calibration means includes means for calibrating the fluid pressure applied to forcibly move said tibia- and condyle-engaging members relative to one another.

12. A knee distraction device according to claim 10 wherein one of said guide members is tubular-shaped and is fixedly attached to the tibia-engaging member and the other of said guide members is fixedly attached to the condyle-engaging member and is configured to slidably move along the inside of the tubular-shaped member, said guide members forming a fluid pressure space in said tubular member for the application of the fluid pressure, and wherein said calibration means includes calibration valve means interposed between the fluid pressure space and a supply of fluid under pressure.

13. A knee distraction device according to claim 12 wherein low-friction lining means are provided in said tubular-shaped guide member to minimize the frictional resistance to relative sliding movement of the guide members with respect to one another.

* * * * *